United States Patent [19]
Estok

[11] Patent Number: 6,001,845
[45] Date of Patent: Dec. 14, 1999

[54] COMBINATION OF PHENTOLAMINE AND APOMORPHINE FOR THE TREATMENT OF HUMAN SEXUAL FUNCTION AND DYSFUNCTION

[75] Inventor: Thomas Mark Estok, Plainfield, N.J.

[73] Assignee: Schering Corporation, Kenilworth, N.J.

[21] Appl. No.: 09/330,112

[22] Filed: Jun. 10, 1999

Related U.S. Application Data

[60] Provisional application No. 60/089,910, Jun. 19, 1998.
[51] Int. Cl.⁶ .......................... A61K 31/44; A61K 31/415
[52] U.S. Cl. ............................................ 514/284; 514/400
[58] Field of Search ...................................... 514/284, 400

[56] References Cited

U.S. PATENT DOCUMENTS

| | | | |
|---|---|---|---|
| 4,521,421 | 6/1985 | Foreman | 514/267 |
| 5,576,290 | 11/1996 | Hadley | 514/11 |
| 5,773,457 | 6/1998 | Nahoum | 514/397 |

*Primary Examiner*—Raymond Henley, III
*Attorney, Agent, or Firm*—Joseph T. Majka; Joanne P. Will

[57] ABSTRACT

A method of treating sexual dysfunction comprising administering a therapeutically effective amount of a combination of phentolamine and apomorphine, as well as pharmaceutical compositions and kits useful in those methods, are disclosed.

11 Claims, No Drawings

COMBINATION OF PHENTOLAMINE AND APOMORPHINE FOR THE TREATMENT OF HUMAN SEXUAL FUNCTION AND DYSFUNCTION

This application claims priority under 35 USC 119(e) over provisional application No. 60/089,910 filed Jun. 19, 1998.

BACKGROUND

The present invention relates to pharmaceutical compositions comprising a combination of phentolamine and apomorphine and to methods of treating sexual dysfunction, including erectile dysfunction, comprising administering an effective amount of a combination of phentolamine and apomorphine.

The use of the pharmaceutical compositions and methods of this invention results in an unexpected potentiation of human sexual response.

SUMMARY OF THE INVENTION

In one embodiment, the present invention is directed to a pharmaceutical composition for the treatment of human sexual dysfunction comprising a therapeutically effective amount of phentolamine or a pharmaceutically acceptable salt, solvate, hydrate, crystalline polymorph form or free base thereof, and a therapeutically effective amount of apomorphine or a pharmaceutically acceptable salt, solvate or hydrate thereof, and a pharmaceutically acceptable carrier.

In a second embodiment, the present invention is directed to a method of treating sexual dysfunction, especially male erectile dysfunction, comprising administering to a human in need of such treatment an effective amount of a combination of phentolamine or a pharmaceutically acceptable salt, solvate, hydrate, crystalline polymorph form or free base thereof, and apomorphine or a pharmaceutically acceptable salt, solvate or hydrate thereof, and a pharmaceutically acceptable carrier. Phentolamine and apomorphine may be administered either substantially concurrently in separate dosage forms or combined in a unit dosage form as described for the pharmaceutical composition above. Preferably, the separate dosage forms and the unit dosage form of the above pharmaceutical composition are designed for oral administration.

In a third embodiment, the invention relates to a kit comprising in one container an effective amount of phentolamine or a pharmaceutically acceptable salt, solvate, hydrate, crystalline polymorph form or free base thereof in a pharmaceutically acceptable carrier, and in a separate container, an effective amount of apomorphine or a pharmaceutically acceptable salt, solvate or hydrate thereof in a pharmaceutically acceptable carrier.

Phentolamine mesylate or phentolamine hydrochloride and apomorphine hydrochloride are the preferred active ingredients for use in the pharmaceutical composition, method of treatment, and use in the kits of this invention.

DETAILED DESCRIPTION

Humans include, of course, males and females. Although the pharmaceutical compositions of the present invention are envisaged primarily for the treatment of erectile dysfunction or male sexual dysfunction, they may also be useful for the treatment of female sexual dysfunction. Such female sexual dysfunction may include orgasmic dysfunction due to clitoral irregularities or disturbances, as well as arousal disorder, which is the inability to engorge and/or lubricate the vaginal wall.

Phentolamine, 3-[[(4,5-dihydro-1H-imidazol-2-yl)methyl](4-methylphenyl)amino]phenol, and pharmaceutically acceptable salts, solvates, hydrates, crystalline polymorph forms and the free base thereof, are useful in the treatment of sexual dysfunction. A rapidly disintegrating tablet and method of use to treat sexual dysfunction is disclosed in U.S. Pat. No. 5,731,339, also incorporated herein by reference. Representative formulations comprising phentolamine are disclosed in U.S. Pat. No. 5,731,339. Phentolamine can exist in unsolvated as well as solvated forms, including hydrated forms, e.g. hemi-hydrate. In general, the solvated forms, with pharmaceutically acceptable solvents such as water, ethanol and the like are equivalent to the unsolvated forms for purposes of the invention. Phentolamine can form pharmaceutically acceptable salts with organic and inorganic acids. Examples of suitable acids for salt formation are hydrohalic acids such as hydrochloric and hydrobromic; as well as other acids such as sulfuric, phosphoric, acetic, citric, oxalic, malonic, salicylic, malic, fumaric, succinic, ascorbic, maleic, methanesulfonic, toluenesulfonic and other mineral and carboxylic acids known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base form for purposes of this invention. Phentolamine can also form crystalline polymorph forms or crystalline forms thereof using suitable or conventional crystallization procedures.

Apomorphine is a synthetic opiate obtained by treating morphine with concentrated hydrochloric acid (Hcl) as described in Small et al., J. Org. Chem. 5, 344 (1940) or by heating morphine with zinc chloride ($ZnCl_2$) as described in Mayer, Ber. 4, 121 (1871). Information on formulations comprising apomorphine are disclosed in U.S. Pat. No. 3,717,639.

Apomorphine and phentolamine are each known to treat sexual dysfunction. The effectiveness of phentolamine for treatment of sexual dysfunction is demonstrated by test procedures described in U.S Pat. No. 5,731,339. Similar procedures can be used to determine the effectiveness of apomorphine and combinations of phentolamine and apomorphine.

Phentolamine and apomorphine (i.e. the active ingredient components of a combination) may be administered either substantially concurrently in separate dosage forms or combined in a unit dosage form. Preferably, the separate dosage forms and the unit dosage form of the above pharmaceutical composition are designed for oral administration. The components of the combination can be administered individually or together in any conventional oral dosage form such as a capsule, tablet, chewable tablets, powder, cachet, suspension or solution. Thus, the pharmaceutical composition of the present invention may administered orally by swallowing. Alternatively, the pharmaceutical composition may be administered parenterally, e.g. sublingually or buccally. The formulations can be prepared using conventional pharmaceutical excipients and additives using conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. A typical formulation for phentolamine comprises about five (5), ten (10), twenty (20), forty (40) or eighty (80) milligrams (mg) of active ingredient or a pharmaceutically acceptable salt, solvate, hydrate, crystalline polymorph form or free base thereof.

In one embodiment, the two active ingredients are administered as a single composition, the dosage forms as disclosed in the aforementioned patent or application may readily be modified using the knowledge of one skilled in the art.

A typical formulation for apomorphine comprises one-quarter (0.25), one-half (0.5), one (1), two (2), three (3), four (4), five (5) or six (6) milligrams (mg) of active ingredient or a pharmaceutically acceptable salt, solvate or hydrate thereof. Inactive ingredients may include microcrystalline cellulose, anhydrous dibasic calcium phosphate, croscarmellose sodium, magnesium stearate, hydroxypropylmethylcellulose, titanium dioxide, lactose, triacetin, and FD&C Blue #2 aluminum lake.

A typical formulation for phentolamine is as follows:

| Component | mg/Tablet (w/w %) |
|---|---|
| phentolamine mesylate, USP | 40 (10) |
| Microcrystalline Cellulose, NF | 341.6 (85.4) |
| Croscarmellose Sodium, NF | 16 (4.0) |
| Colloidal Silicon Dioxide, NF | 0.4 (0.1) |
| Magnesium Stearate, NF | 2 (0.5) |
| Total | 400 (100) |

The following are exemplary formulations for the phentolamine mesylate/apomorphine hydrochloride combination:

Direct Compression Formulation

| Component | mg/Tablet |
|---|---|
| Phentolamine Mesylate | 80 |
| Apomorphine hydrochloride | 2 |
| Microcrystalline Cellulose | 207.5–209.0 |
| Croscarmellose Sodium | 10 |
| Silicon Dioxide | 0.5 |
| Magnesium Stearate | 0.5–2 |
| Total | 302 |

The direct-compression formulation is manufactured by blending the active ingredients and excipients and compressing the mixture into tablets.

Wet-Granulation Formulation

| Component | mg/Tablet |
|---|---|
| Phentolamine Mesylate | 80 |
| Apomorphine | 3 |
| Microcrystalline Cellulose | 80 |
| Lactose | 114–115.5 |
| Sodium Starch Glycolate | 12 |
| Povidone | 12 |
| Water | (evaporates) |
| Magnesium Stearate | 0.5–2 |
| Total | 303 |

The wet-granulation formulation is manufactured using the following steps:

1. the active ingredients are combined with microcrystalline cellulose, lactose and sodium starch glycolate in a mixer/granulator;
2. povidone is added to water to form a solution;
3. the granulating solution (from step 2) is added to the powder blend (from step 1) with agitation to form a granulation, and the resulting granulation is dried;
4. the dry granulation is blended with magnesium stearate; and
5. the mixture is compressed into tablets.

Fast-Dissolving Formulations

A

| Component | mg/Tablet |
|---|---|
| Phentolamine Mesylate | 40 |
| Apomorphine hydrochloride | 1 |
| Gelatin | 30 |
| Mannitol | 29 |
| Flavor | 1 |
| Water | (evaporates) |
| Total Dry Tablet Weight | 101 |

The above tablet form is manufactured by:
1. forming a uniform dispersion achieved by adding the active ingredients and excipients to water with agitation;
2. filling aliquots of the dispersion into molds; and
3. lyophilizing to form dry tablets.

B

| Component | mg/Tablet |
|---|---|
| Phentolamine Mesylate | 40 |
| Apomorphine | 0.5 |
| Microcrystalline Cellulose | 95 |
| Crospovidone | 10 |
| Sodium Bicarbonate | 2 |
| Citric Acid | 2 |
| Flavor | 1 |
| Total | 150.5 |

The tablets are made by blending the combination of the actives and excipients and compressing the mixture into tablets.

The compounds in the combination of this invention for treating sexual dysfunction can be administered in accordance with the treatment regimens described in each of the above listed publications. For example, for a combination of apomorphine in combination with phentolamine, the typical dosage is about 0.25 to about 6 mg of apomorphine and about 5 to about 80 mg of phentolamine per dose, usually administered approximately 30 minutes before anticipated intercourse. It is expected that the dosage of the individual components in the combination will be less than the dosage required when the individual components are administered alone. The exact dose of either component, i.e. active ingredient, of the combination to be administered and the timing thereof is determined by the attending clinician and is dependent on the potency of the compound administered, the age, weight, condition and response of the patient. Where the components of a combination are administered separately, the separate dosage forms can be administered at about the same time or at different dosage intervals.

Since the present invention relates to treatment with a combination of active ingredients wherein said active ingredients may be administered separately, the invention also relates to combining separate pharmaceutical compositions in kit form. That is, a kit is contemplated wherein two separate unit dosage forms are combined: for example, an apomorphine pharmaceutical composition and a phentolamine pharmaceutical composition. The kit will preferably include directions for the administration of the separate components. The kit form is particularly advantageous when the separate components must be administered in different dosage forms (e.g. tablet and capsule) and/or are administered at different dosage intervals. Thus, a kit may comprise, in separate containers in a single package, pharmaceutical compositions for use in combination to treat sexual dysfunction which comprises in one container a therapeutically effective amount of phentolamine or a pharmaceutically acceptable salt, solvate, hydrate, crystalline polymorph form or free base thereof in a pharmaceutically acceptable carrier and in a second container a therapeutically effective amount of apomorphine or a pharmaceutically acceptable salt, solvate or hydrate thereof in a pharmaceutically acceptable carrier.

What is claimed is:

1. A pharmaceutical composition for the treatment of human sexual dysfunction comprising a therapeutically effective amount of phentolamine or a pharmaceutically acceptable salt, solvate, hydrate, crystalline polymorph form or free base thereof, and a therapeutically effective amount of apomorphine or a pharmaceutically acceptable salt, solvate or hydrate thereof, and a pharmaceutically acceptable carrier.

2. The composition of claim 1 wherein the phentolamine is phentolamine mesylate.

3. The composition of claim 1 wherein the phentolamine is phentolamine hydrochloride.

4. The composition of claim 1 wherein the apomorphine is apomorphine hydrochloride.

5. The composition of claim 1 wherein the phentolamine is phentolamine mesylate and apomorphine is apomorphine hydrochloride.

6. A kit comprising in separate containers in a single package, pharmaceutical compositions for use in combination to treat sexual dysfunction which comprises in one container a therapeutically effective amount of phentolamine or a pharmaceutically acceptable salt, solvate, hydrate, crystalline polymorph form or free base thereof in a pharmaceutically acceptable carrier and in a second container a therapeutically effective amount of apomorphine or a pharmaceutically acceptable salt, solvate or hydrate thereof in a pharmaceutically acceptable carrier.

7. A method of treating sexual dysfunction, especially male erectile dysfunction, comprising administering to a human in need of such treatment an effective amount of a combination of phentolamine or a pharmaceutically acceptable salt, solvate, hydrate, crystalline polymorph form or free base thereof, and apomorphine or a pharmaceutically acceptable salt, solvate or hydrate thereof, and a pharmaceutically acceptable carrier, wherein said phentolamine and said apomorphine are administered either substantially concurrently in separate dosage forms or combined in a unit dosage form.

8. The method of claim 7 wherein the phentolamine is phentolamine mesylate.

9. The method of claim 7 wherein the phentolamine is phentolamine hydrochloride.

10. The method of claim 8 wherein the apomorphine is apomorphine hydrochloride.

11. The method of claim 7 wherein the phentolamine is phentolamine mesylate and apomorphine is apomorphine hydrochloride.

* * * * *